United States Patent [19]

Los et al.

[11] Patent Number: 4,709,036
[45] Date of Patent: Nov. 24, 1987

[54] PROCESS FOR THE PREPARATION OF HERBICIDAL 2-(4,4-DISUBSTITUTED-5-OXO-2-IMIDAZO-LIN-2-YL)BENZOIC, NICOTINIC AND QUINOLINE-3-CARBOXYLIC ACIDS, ESTERS AND SALTS

[75] Inventors: Marinus Los, Pennington; Don W. Long; Gregory P. Withers, both of Lawrenceville, all of N.J.

[73] Assignee: American Cyanamid Company, Stamford, Conn.

[21] Appl. No.: 744,705

[22] Filed: Jun. 13, 1985

[51] Int. Cl.$^4$ .................. C07D 401/04; C07D 233/32
[52] U.S. Cl. .................................. 546/167; 546/278; 546/170; 546/318; 548/301; 548/347; 548/348; 548/351; 558/392
[58] Field of Search .............. 546/167, 278; 548/301, 548/347, 351

[56] References Cited

U.S. PATENT DOCUMENTS

| 3,721,679 | 3/1973 | Singer | 548/301 |
| 4,188,487 | 2/1980 | Los | 548/301 |
| 4,213,986 | 7/1980 | Gebert et al. | 596/278 |
| 4,518,780 | 5/1985 | Barton et al. | 546/278 |
| 4,544,754 | 10/1985 | Los | 548/301 |

FOREIGN PATENT DOCUMENTS

| 8304252 | 5/1983 | European Pat. Off. | 546/278 |
| 0133311 | 2/1985 | European Pat. Off. | 71/92 |
| 0225179 | 12/1984 | Japan | 546/167 |

Primary Examiner—Glennon H. Hollrah
Assistant Examiner—D. B. Springer
Attorney, Agent, or Firm—H. G. Jackson

[57] ABSTRACT

The present invention provides a process for the preparation of herbicidal 2-(4,4-disubstituted-5-oxo-2-imidazolin-2-yl) benzoic, nicotinic and quinoline-3-carboxylic acids, esters and salts.

12 Claims, No Drawings

PROCESS FOR THE PREPARATION OF HERBICIDAL 2-(4,4-DISUBSTITUTED-5-OXO-2-IMIDAZOLIN-2-YL)BENZOIC, NICOTINIC AND QUINOLINE-3-CARBOXYLIC ACIDS, ESTERS AND SALTS

BACKGROUND OF THE INVENTION

Herbicidal 5-oxo-imidazolinyl benzoic acids, esters and salts, their preparation and use are disclosed in U.S. Pat. No. 4,188,487 and U.S. Pat. No. 4,297,128 and pending applications for United States Patents Ser. No.: 823,863 01/29/86, cont. of 579,224, 02/10/84, abandoned; 631,283, 07/16/84, U.S. Pat. No. 4,554,013; Ser. No. 629/296, 07/09/84; 382,041, 05/25/82, U.S. Pat. No. 4,638,068; Ser. No. 616,747, 06/04/84, U.S. Pat. No. 4,647,301.

The free acids of these compounds may be represented in general by Formula I below

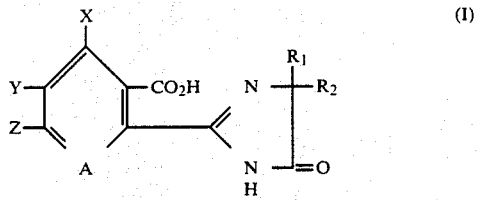

wherein
A is $CR_3$ or N;
$R_1$ and $R_2$ each represent $C_1$-$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$-$C_6$ cycloalkyl ring optionally substituted with methyl;
X is hydrogen, halogen or methyl;
Y and Z are each hydrogen, halogen, $C_1$-$C_6$ alkyl, $C_1$-$C_4$ hydroxyalkyl, $C_1$-$C_6$ alkoxy, $C_1$-$C_4$ alkylthio, phenoxy, $C_1$-$C_4$ haloalkyl, $OCF_2CHF_2$, $OCF_3$, $OCHF_2$, nitro, cyano, $C_1$-$C_4$ alkylsulfonyl, $NR_4R_5$; $C_3$-$C_8$ straight or branched alkenyloxy optionally substituted with one to three halogens, $C_3$-$C_8$ straight or branched alkynyloxy optionally substituted with one to three halogens, or phenyl optionally substituted with one or two $C_1$-$C_4$ alkyl, $C_1$-$C_4$ alkoxy or halogen or combinations of any two of these groups;
$R_3$ is hydrogen, halogen, $C_1$-$C_4$ alkyl, $C_1$-$C_4$ alkylthio, $C_1$-$C_4$ alkoxy, $CF_3$, $NO_2$, $OCF_3$, $OCHF_2$ or $OCF_2CHF_2$;
$R_4$ is hydrogen or $C_1$-$C_4$ alkyl;
$R_5$ is $C_1$-$C_4$ alkyl;
and, when taken together, Y and Z may form a ring in which YZ is represented by
(1) the structure: —$(CH_2)_n$—, where n is an integer of 2, 3 or 4; or
(2) by the structure:

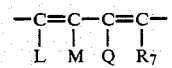

L, M, Q and $R_7$ are each hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, difluoromethoxy, trifluoromethoxy, 1,1,2,2-tetrafluoroethoxy, $NO_2$, CN, phenyl, phenoxy, amino, $C_1$-$C_4$ alkylamino, diloweralkylamino, chlorophenyl, methylphenyl, phenoxy substituted with one Cl, $CF_3$, $NO_2$ or $CH_3$ group, $C_3$-$C_8$ straight or branched alkenyloxy optionally substituted with one to three halogens, or $C_3$-$C_8$ straight or branched alkynyloxy optionally substituted with one to three halogens;
the N-oxides thereof when A is N provided that Y or Z cannot be alkylamino, dialkylamino or alkylthio;
the optical isomers thereof when $R_1$ and $R_2$ are not the same;
the tautomers thereof; and
the acid addition salts thereof.

Preparation of the above-identified formula I N-oxides can be achieved following the procedures described in European Patent Application Number 81103638.3, publication number 0,041,623, incorporated herein by reference thereof.

It is an object of this invention to provide a novel process for the preparation of herbicidal imidazolinyl benzoic, nicotinic and quinoline-3-carboxylic acids of Formula I and the herbicidal esters and salts of these acids.

SUMMARY OF THE INVENTION

The invention is a novel process for the preparation of herbicidal 5-oxo-imidazolinyl benzoic, nicotinic and quinoline-3-carboxylic acids of Formula I

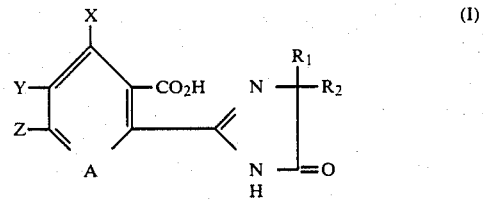

wherein A, X, Y, Z, $R_1$, $R_2$ and $R_3$ are as described above or herbicidal esters and salts thereof comprising reacting an N-(1-cyano-1,1-disubstituted methyl)phthalamic acid, or a 2-[(1-cyano-1,1-disubstituted methyl)carbamoyl]nicotinic or quinoline-3-carboxylic acid of Formula II

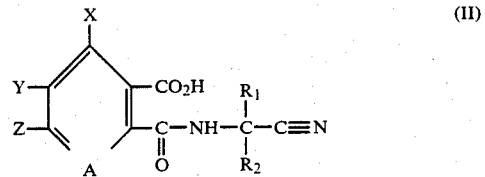

wherein A, X, Y, Z, $R_1$, $R_2$ and $R_3$ are as described for Formula I, in a chlorinated hydrocarbon saturated with an excess of a hydrogen halide, preferably hydrogen chloride, in a temperature range of 0° C. to 130° C. and preferably 20° C. to 40° C. for from 1 to 20 hours under anhydrous conditions.

Additionally, it has been found that the yield of 5-oxo-imidazolinyl products may be improved by the further conversion of the major by-product in the above reaction mixture which is an amide of Formula III, by dehydration of the resulting reaction mixture, thermally or in the presence of an acid catalyst, followed by reaction of the thus formed Formula IV dione with water or an alcohol in the presence of an acid or base as illustrated in Flow Diagram I below:

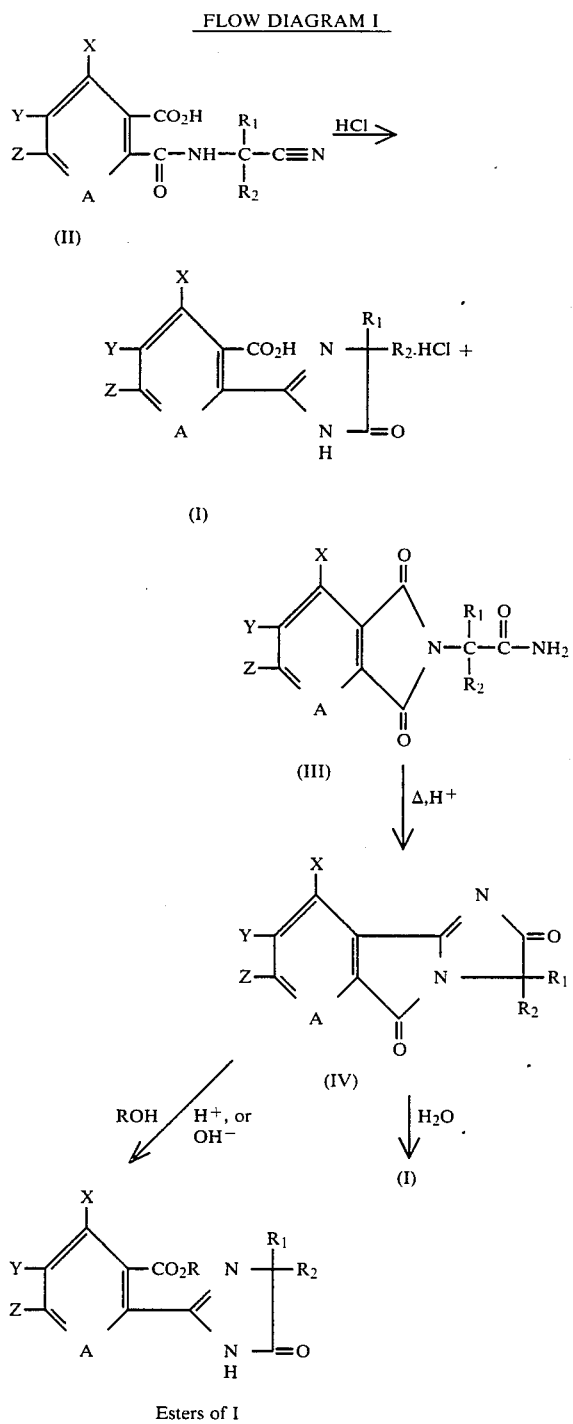

Esters of I wherein A, X, Y, Z, $R_1$, $R_2$ and $R_3$ are as described for Formula I above. Preferred chlorinated hydrocarbon solvents for use in the process of the invention include dichloromethane, 1,2-dichloroethane and o-dichlorobenzene. Acids such as p-toluenesulfonic, naphthalenesulfonic, sulfuric, trifluoroacetic acid are among the acids suitable for use in the dehydration of the Formula III amide, the water being removed from the reaction continuously by distillation. The process of the reaction thus provides a method for the preparation of Formula I imidazolinyl benzoic, nicotinic, and quinoline-3-carboxylic acids as the hydrochloride salt in one step by cooling the initial reaction and filtering off the product as the salt. The filtrate containing the Formula III amide as the major component may then be dehydrated and reacted with water or an alcohol as described above.

Alternatively, the reactions illustrated in Flow Diagram I may be conducted as an integrated reaction sequence by reaction of a Formula II compound with an excess of hydrogen halide in a chlorinated hydrocarbon under anhydrous conditions until the reaction is complete, followed by dehydration in the presence of a catalytic amount of an acid such as p-toluenesulfonic which may then be added and the reaction mixture brought to reflux and water removed by azeotropic distillation. The reaction mixture is then cooled to room temperature and water or an alcohol added and the resulting mixture reacted under either acid or basic conditions in a temperature in the range of 20° C. to 50° C. until the formation of the desired acid or ester is essentially complete, usually 4 to 24 hours. When acid conditions are employed the products are obtained as the acid addition salts.

The process of the invention is further illustrated by the following non-limiting examples.

EXAMPLE 1

Preparation of 0-(4-isopropyl-4-methyl-5-oxo-2-imidazolin-2-yl)-benzoic acid, hydrochloride

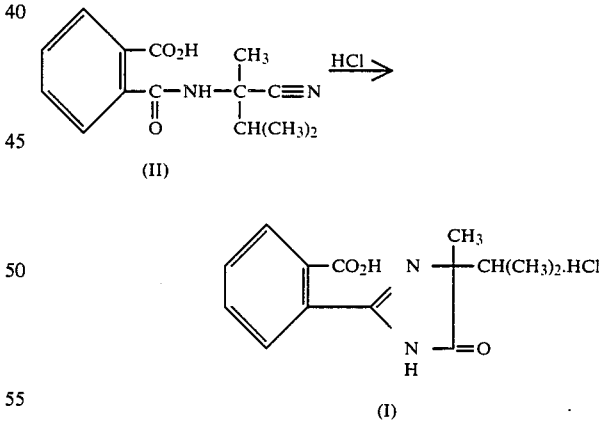

Hydrogen chloride gas is added to a slurry of 5.0 g (0.019 mole) N-(1-cyano-1,2-dimethylpropyl)phthalamic acid in 95 ml o-dichlorobenzene. The gas is added over 15 minutes at 25° C. until it is no longer absorbed. The mixture is stirred for 17 hours at 20°–25° C., and the resulting solid then filtered off. The filtered solid is washed with 1,2-dichloroethane and dried to give 2.33 g (41.3%) o-(4-isopropyl-4-methyl-5-oxo-2-imidazolin-2-yl)-benzoic acid, hydrochloride, melting point 232°–245° C.

EXAMPLE 2

Preparation of o-(4-isopropyl-4-methyl-5-oxo-2-imidazolin-2-yl)benzoic acid, methyl ester

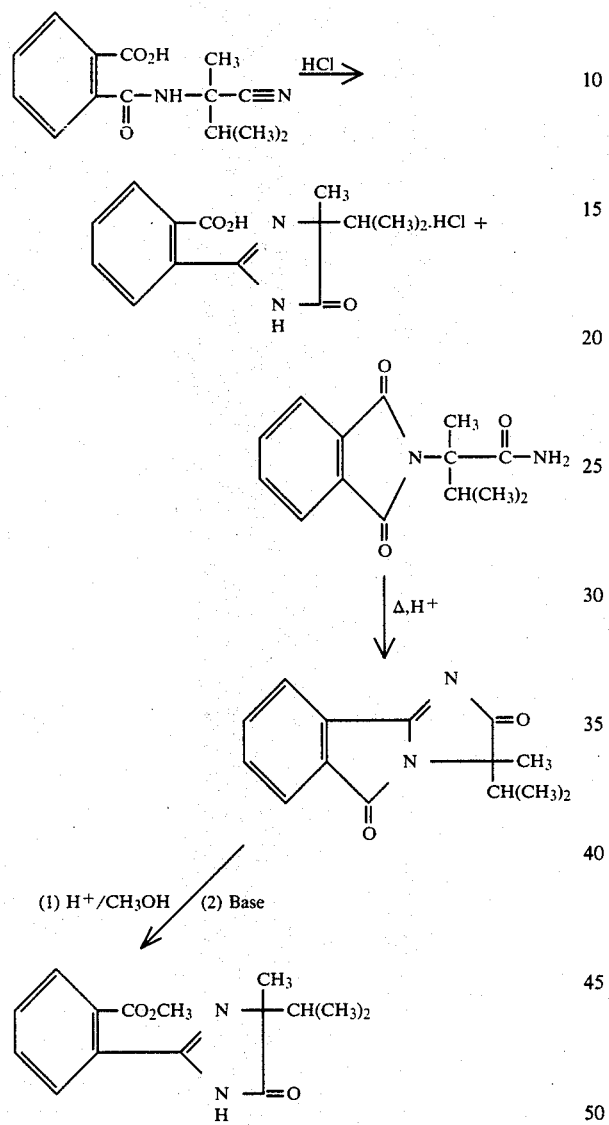

Hydrogen chloride gas is added to a slurry of 10.0 g (0.038 mole) N-(1-cyano-1,2-dimethylpropyl)phthalamic acid in 125 mL o-dichlorobenzene. The gas is added over 30 minutes at 25° C. until it is no longer absorbed. The mixture is stirred for 12 hours at 20°–25° C. A sample analyzed by thin layer chromatography indicates the starting material is converted to a mixture of o-(4-isopropyl-4-methyl-5-oxo-2-imidazolin-2-yl)-benzoic acid hydrochloride and α,β-dimethyl-α-phthalimidobutyramide.

Then 0.73 g (0.0038 mole) p-toluenesulfonic acid monohydrate is added and the mixture is heated to 140° C. and stirred at 140° C. for 5 hours while water is separated in a trap. The mixture is cooled to 25° C. A sample is analyzed by a thin layer chromatography and contains 3-isopropyl-3-methyl-5H-imidazo[2,1-a]isoindole-2(3H), 5-dione as the major product and a minor amount of unreacted o-(5-isopropyl-5-methyl-4-oxo-2-imidazolin-2-yl)-benzoic acid hydrochloride.

Methanol (25 mL) and additional hydrogen chloride gas are added at 20°–30° C. The reaction mixture is stirred at 50° C. for 23 hours and methanol is evaporated off under vacuum. The resulting slurry is filtered and the solid washed with n-hexane. After drying, the solid, 10.2 g, is analyzed by thin layer chromatography and is found to be o-(4-isopropyl-4-methyl-5-oxo-2-imidazolin-2-yl)-benzoic acid, methyl ester hydrochloride. The overall yield is 85.4%.

The hydrochloride is stirred with 60 mL water and 80 mL dichloromethane. Solid sodium bicarbonate is added until a pH of 7 is obtained. The organic layer is separated, washed with water and dried over anhydrous magnesium sulfate. The magnesium sulfate is removed by filtration and the filtrate evaporated to leave a crude solid. The solid is recrystallized from an acetone/n-hexane mixture to give 6.3 g (60.4%) of o-(4-isopropyl-4-methyl-5-oxo-2-imidazolin-2-yl)-benzoic acid, methyl ester, melting point 113°–114° C.

EXAMPLE 3

Preparation of 2-(4-isopropyl-4-methyl-5-oxo-2-imidazolin-2-yl)nicotinic acid

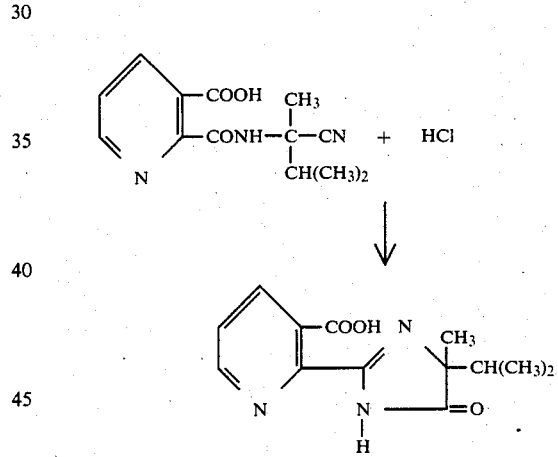

A stirred solution containing 2-[(1-cyano-1,2-dimethylpropyl)carbamoyl]nicotinic acid (5.0 g, 0.02 mol) in 150 mL of dry o-dichlorobenzene under a nitrogen atmosphere at room temperature is purged with hydrogen chloride gas for 15 minutes. The mixture is heated to 110° C. for 16 hours, cooled to room temperature and the resulting solid removed by filtration. The filter cake is washed with 200 ml dry ethylenedichloride and dried in vacuo at 75° C. for three hours to give 3.5 g of a gray solid, which is assayed by liquid chromatography and shown to contain 13.3% of the title product.

Utilizing the above procedure and substituting the 2-[(1-cyano-1,2-dimethylpropyl)carbamoyl]-5-ethylnicotinic acid or 2-[(1-cyano-1,2-dimethylpropyl)carbamoyl]-5-methylnicotinic acid for 2-[(1-cyano-1,2-dimethylpropyl)carbamoyl]nicotinic acid yields the appropriately substituted 2-(4-isopropyl-4-methyl-5-oxo-2-imidazolin-2-yl)-5-substituted nicotinic acid.

EXAMPLE 4

Preparation of 2-(4-isopropyl-4-methyl-5-oxo-2-imidazolin-2-yl)-3-quinolinecarboxylic acid

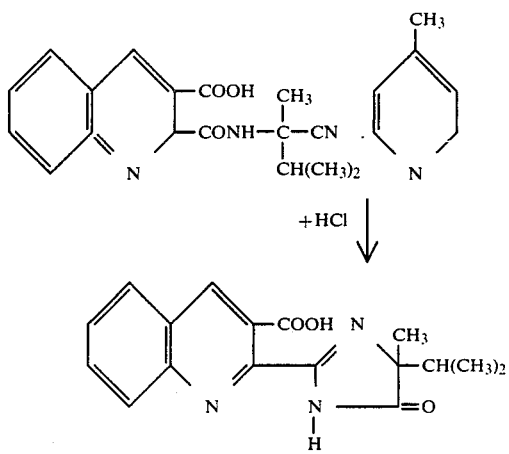

A stirred mixture containing the 4-picoline salt of 2-[(1-cyano-1,2-dimethylpropyl)carbamoyl]-3-quinolinecarboxylic acid (8.0 g, 0.02 mol) in 200 mL of dry o-dichlorobenzene under $N_2$ at room temperature is purged with hydrogen chloride gas for 15 minutes. The mixture is heated to 85° C. for 72 hours, cooled to room temperature and the resulting solid is removed by filtration. The filter cake is washed with 200 mL dry ethylenedichloride and dried in vacuo at 75° C. for three hours to give 3.7 g (52.8%) of a soft grey solid, which is assayed by liquid chromatography and shown to contain 19.8% of 2-(4-isopropyl-4-methyl-5-oxo-2-imidazolin-2-yl)-3-quinolinecarboxylic acid. A similar result is obtained when 2-[(1-cyano-1,2-dimethylpropyl)carbamoyl]-3-quinolinecarboxylic acid is employed in place of the picoline salt.

What is claimed is:

1. A process for the preparation of herbicidal 5-oxo-imidazolinyl benzoic, nicotinic and quinoline-3-carboxylic acids of Formula I

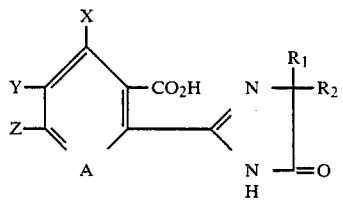

wherein
A is $CR_3$ or N;
$R_1$ and $R_2$ each represent $C_1$–$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$–$C_6$ cycloalkyl ring optionally substituted with methyl;
X is hydrogen, halogen or methyl;
Y and Z are each hydrogen, halogen, $C_1$–$C_6$ alkyl, $C_1$–$C_4$ hydroxyalkyl, $C_1$–$C_6$ alkoxy, $C_1$–$C_4$ alkylthio, phenoxy, $C_1$–$C_4$ haloalkyl, $OCF_2CHF_2$; $OCF_3$, $OCHF_2$, nitro, cyano, $C_1$–$C_4$ alkylsulfonyl, $NR_4R_5$, $C_3$–$C_8$ straight or branched alkenyloxy optionally substituted with one to three halogens, $C_3$–$C_8$ straight or branched alkynyloxy optionally substituted with one to three halogens, or phenyl optionally substituted with one to two $C_1$–$C_4$ alkyl, $C_1$–$C_4$ alkoxy or halogen or combinations of any two of these groups;
$R_3$ is hydrogen, halogen, $C_1$–$C_4$ alkyl, $C_1$–$C_4$ alkylthio, $C_1$–$C_4$ alkoxy, $CF_3$, $NO_2$, $OCF_3$, $OCHF_2$ or $OCF_2CHF_2$;
$R_4$ is hydrogen or $C_1$–$C_4$ alkyl;
$R_5$ is $C_1$–$C_4$ alkyl;
and, when taken together, Y and Z may form a ring in which YZ is represented by
(1) the structure: —$(CH_2)_n$—, where n is an integer of 2, 3 or 4; or
(2) by the structure:

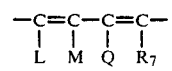

L, M, Q and $R_7$ are each hydrogen, halogen, $C_1$–$C_4$ alkyl, $C_1$–$C_4$ alkoxy, $C_1$–$C_4$ alkylthio, $C_1$–$C_4$ alkylsulfonyl, $C_1$–$C_4$ haloalkyl, difluoromethoxy, trifluoromethoxy, 1,1,2,2-tetrafluoroethoxy, $NO_2$, CN, phenyl, phenoxy, amino, $C_1$–$C_4$ alkylamino, diloweralkylamino, chlorophenyl, methylphenyl, phenoxy substituted with one Cl, $CF_3$, $NO_2$, or $CH_3$ group, $C_3$–$C_8$ straight or branched alkenyloxy optionally substituted with one to three halogens, or $C_3$–$C_8$ straight or branched alkynyloxy optionally substituted with one to three halogens;
the optical isomers thereof when $R_1$ and $R_2$ are not the same;
the tautomers thereof; and
the acid addition salts thereof or herbicidal esters and salts thereof comprising reacting an N-(1-cyano-1,1-disubstituted methyl)phthalamic acid, or a 2-[(1-cyano-1,1-disubstituted methyl)carbamoyl]-nicotinic or quinoline-3-carboxylic acid of Formula II

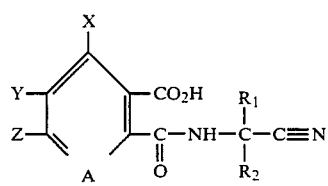

wherein A, X, Y, Z, $R_1$, $R_2$ and $R_3$ are as described for Formula I, in a chlorinated hydrocarbon saturated with an excess of a hydrogen halide, in a temperature range of 0° C. to 130° C. for from one to 20 hours under anhydrous conditions.

2. A process according to claim 1 wherein the solvent is dichloromethane, 1,2-dichloroethane, or o-dichlorobenzene and the hydrogen halide is hydrogen chloride.

3. A process according to claim 2 wherein A is $CR_3$.

4. A process according to claim 2 wherein A is nitrogen.

5. A process according to claim 3 for the preparation of a herbicidal isomeric mixture of 6-(4-isopropyl-4-methyl-5-oxo-2-imidazolin-2-imidazolin-2-yl)-m-toluic acid, and 2-(4-isopropyl-4-methyl-5-oxo-2-imidazolin-2-yl-p-toluic acid, and the methyl esters thereof.

6. A process according to claim 4 for the preparation of 2-(4-isopropyl-4-methyl-5-oxo-2-imidazolin-2-yl)-3-quinolincarboxylic acid, 2-(4-isopropyl-4-methyl-5-oxo-2-imidazolin-2-yl)nicotinic acid, 5-ethyl-2-(4-isopropyl-4-methyl-5-oxo-2-imidazolin-2-yl)nicotinic acid, and the esters and salts thereof.

7. A process for the preparation of herbicidal 5-oxo-imidazolinyl benzoic, nicotinic and quinoline-3-carboxylic acids of Formula I

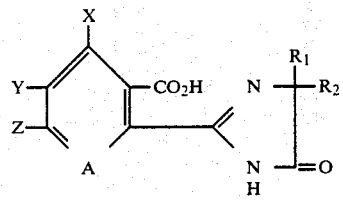

wherein

A is $CR_3$ or N;

$R_1$ and $R_2$ each represent $C_1$–$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$–$C_6$ cycloalkyl ring optionally substituted with methyl;

X is hydrogen, halogen or methyl;

Y and Z are each hydrogen, halogen, $C_1$–$C_6$ alkyl, $C_1$–$C_4$ hydroxyalkyl, $C_1$–$C_6$ alkoxy, $C_1$–$C_4$ alkylthio, phenoxy, $C_1$–$C_4$ haloalkyl, $OCF_2CHF_2$; $OCF_3$, $OCHF_2$, nitro, cyano, $C_1$–$C_4$ alkylsulfonyl, $NR_4R_5$, $C_3$–$C_8$ straight or branched alkenyloxy optionally substituted with one to three halogens, $C_3$–$C_8$ straight or branched alkynyloxy optionally substituted with one to three halogens, or phenyl optionally substituted with one to two $C_1$–$C_4$ alkyl, $C_1$–$C_4$ alkoxy or halogen or combinations of any two of these groups;

$R_3$ is hydrogen, halogen, $C_1$–$C_4$ alkyl, $C_1$–$C_4$ alkylthio, $C_1$–$C_4$ alkoxy, $CF_3$, $NO_2$, $OCF_3$, $OCHF_2$ or $OCF_2CHF_2$;

$R_4$ is hydrogen or $C_1$–$C_4$ alkyl;

$R_5$ is $C_1$–$C_4$ alkyl;

and, when taken together, Y and Z may form a ring in which YZ is represented by (1) the structure: —$(CH_2)_n$—, where n is an integer of 2, 3 or 4; or
(2) by the structure:

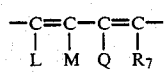

L, M, Q and $R_7$ are each hydrogen, halogen, $C_1$–$C_4$ alkyl, $C_1$–$C_4$ alkoxy, $C_1$–$C_4$ alkylthio, $C_1$–$C_4$ alkylsulfonyl, $C_1$–$C_4$ haloalkyl, difluoromethoxy, trifluoromethoxy, 1,1,2,2-tetrafluoroethoxy, $NO_2$, CN, phenyl, phenoxy, amino, $C_1$–$C_4$ alkylamino, diloweralkylamino, chlorophenyl, methylphenyl, phenoxy substituted with one Cl, $CF_3$, $NO_2$, or $CH_3$ group, $C_3$–$C_8$ straight or branched alkenyloxy optionally substituted with one to three halogens, or $C_3$–$C_8$ straight or branched alkynyloxy optionally substituted with one to three halogens;

the optical isomers thereof when $R_1$ and $R_2$ are not the same;

the tautomers thereof; and the acid addition salts thereof or herbicidal esters and salts thereof comprising reacting an N-(1-cyano-1,1-disubstituted methyl)phthalamic acid, or a 2-[(1-cyano-1,1-disubstituted methyl)ccarbamoyl]-nicotinic or quinoline-3-carboxylic acid of Formula II

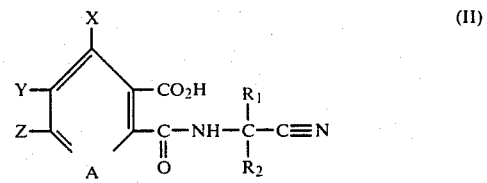

wherein A, X, Y, Z, $R_1$, $R_2$ and $R_3$ are as described for Formula I, in a chlorinated hydrocarbon saturated with an excess of a hydrogen halide, in a temperature range of 0° C. to 130° C. for from one to 20 hours under anhydrous conditions; dehydrating and removing water from the resulting reaction by distillation, optionally in the presence of an acid catalyst; cooling the reaction mixture, followed by reaction with water or an alcohol under acid or basic conditions in a temperature range of 20° C. to 50° C. for from 4 to 24 hours; distilling off the solvent; and filtering off the product.

8. A process according to claim 7 wherein the solvent is dichloromethane, 1,2-dichloroethane, o-di-chlorobenzene; the hydrogen halide is hydrogen chloride, the catalyst is p-toluene sulfonic acid, naphthalenesulfonic acid, or sulfuric acid.

9. A process according to claim 8 wherein A is $CR_3$.

10. A process according to claim 8 wherein A is nitrogen.

11. A process according to claim 9 for the preparation of a herbicidal isomeric mixture of 6-(4-isopropyl-4-methyl-5-oxo-2-imidazolin-2-yl)-m-toluic acid, and 2-(4-isopropyl-4-methyl-5-oxo-2-imidazolin-2-yl-p-toluic acid, and the methyl esters thereof.

12. A process according to claim 10 for the preparation of 2-(4-isopropyl-4-methyl-5-oxo-2-imidazolin-2-yl)-3-quinolincarboxylic acid, 2-(4-isopropyl-4-methyl-5-oxo-2-imidazolin-2-yl)nicotinic acid, 5-ethyl-2-(4-isopropyl-4-methyl-5-oxo-2-imidazolin-2-yl)nicotinic acid, and the esters and salts thereof.

* * * * *